(12) United States Patent
Murphy et al.

(10) Patent No.: US 10,422,732 B2
(45) Date of Patent: Sep. 24, 2019

(54) SENSING CHARACTERISTICS AND A TYPE OF FLUID USING A TEMPERATURE DEPENDENT RATE OF CHANGE OF A MEASUREMENT OF THE FLUID

(71) Applicant: SSI Technologies, Inc., Janesville, WI (US)

(72) Inventors: Gregory P. Murphy, Janesville, WI (US); Mark Edward Kernien, Edgerton, WI (US)

(73) Assignee: SSI Technologies, Inc., Janesville, WI (US)

( * ) Notice: Subject to any disclaimer, the term of this patent is extended or adjusted under 35 U.S.C. 154(b) by 262 days.

(21) Appl. No.: 15/238,936

(22) Filed: Aug. 17, 2016

(65) Prior Publication Data
US 2018/0052086 A1    Feb. 22, 2018

(51) Int. Cl.
*G01F 23/296* (2006.01)
*G01N 11/16* (2006.01)
(Continued)

(52) U.S. Cl.
CPC ........... *G01N 11/16* (2013.01); *G01F 23/246* (2013.01); *G01F 23/2962* (2013.01);
(Continued)

(58) Field of Classification Search
CPC .. G01N 11/16; G01N 29/024; G01N 29/4427; G01F 23/246; G01F 23/2962; G01F 23/30
See application file for complete search history.

(56) References Cited

U.S. PATENT DOCUMENTS

| 5,265,460 A | 11/1993 | Ellinger et al. |
| 2009/0199626 A1 | 8/2009 | Murphy et al. |

(Continued)

FOREIGN PATENT DOCUMENTS

| DE | 10035624 A1 | 2/2002 |
| GB | 968561 A | 9/1964 |

OTHER PUBLICATIONS

International Search Report and Written Opinion for Application No. PCT/US2017/046898 dated Oct. 20, 2017 (16 pages).
(Continued)

*Primary Examiner* — David Z Huang
(74) *Attorney, Agent, or Firm* — Michael Best & Friedrich LLP

(57) ABSTRACT

A system for sensing characteristics of a fluid contained within a tank. The system including an ultrasonic sensor, a temperature sensor, and a controller. The ultrasonic sensor is configured to output a ultrasonic pulse into the fluid, receive an echo of the ultrasonic pulse, and output a signal based on the received echo. The temperature sensor is configured to sense a temperature of the fluid and output a temperature signal corresponding to the temperature of the fluid. The controller is configured to determine a time-of-flight based on the output of the ultrasonic pulse and the received echo of the ultrasonic pulse, receive the temperature signal, determine a characteristic of the fluid based on the time-of-flight and the temperature signal, compare the characteristic of the fluid to a baseline characteristic, and output a signal based on the comparison between the characteristic of the fluid and the baseline characteristic.

13 Claims, 12 Drawing Sheets

(51) Int. Cl.
    *G01F 23/24* (2006.01)
    *G01F 23/30* (2006.01)
    *G01N 29/024* (2006.01)
    *G01N 29/44* (2006.01)
    *G01N 29/32* (2006.01)
(52) U.S. Cl.
    CPC ........... *G01F 23/30* (2013.01); *G01N 29/024* (2013.01); *G01N 29/326* (2013.01); *G01N 29/4427* (2013.01); *G01N 2291/02818* (2013.01)

(56) References Cited

U.S. PATENT DOCUMENTS

| 2012/0118059 A1 | 5/2012 | Reimer et al. |
| 2014/0196536 A1 | 7/2014 | Murphy |
| 2015/0089996 A1* | 4/2015 | Reimer ................. G01N 29/02 73/19.03 |

OTHER PUBLICATIONS

International Preliminary Report on Patentability for Application No. PCT/US2017/046898 dated Feb. 28, 2019 (10 pages).

* cited by examiner

SENSING CHARACTERISTICS AND A TYPE OF FLUID USING A TEMPERATURE DEPENDENT RATE OF CHANGE OF A MEASUREMENT OF THE FLUID

BACKGROUND

The application relates to sensing characteristics of a fluid.

SUMMARY

Various systems require fluids (for example, oil, fuel, diesel exhaust fluid, brake fluid, transmission fluid, washer fluid, refrigerant, etc.). Often, a system requirement is that these fluids have certain characteristics, for example, viscosity, volatility, acidity/alkalinity, and others. For example, internal combustion engines and other mechanical devices require oil having certain characteristics, for example, viscosity. Oils are often graded by viscosity and otherwise classified for particular uses. Using an incorrect oil in an internal combustion engine may damage the engine. Viscosity of fluids, such as oil, are typically measured using specific instruments such as viscometers and rheometers. These meters use glass capillaries, rotation, or vibrations to measure the viscosity. As a consequence, they are generally unsuitable for use in vehicles powered by internal combustion engines, where conditions often include high temperatures and movement.

Therefore, one embodiment provides a system for sensing characteristics of a fluid contained within a tank. The system includes an ultrasonic sensor, a temperature sensor, and a controller. The ultrasonic sensor is configured to output a ultrasonic pulse into the fluid, receive an echo of the ultrasonic pulse, and output a signal based on the received echo. The temperature sensor is configured to sense a temperature of the fluid and output a temperature signal corresponding to the temperature of the fluid. The controller is configured to determine a time-of-flight based on the output of the ultrasonic pulse and the received echo of the ultrasonic pulse. The controller is also configured to receive the temperature signal, determine a characteristic of the fluid based on the time-of-flight and the temperature signal, compare the characteristic of the fluid to a baseline characteristic, and output a signal based on the comparison between the characteristic of the fluid and the baseline characteristic.

Another embodiment provides a method of sensing a characteristic of fluid contained within a sensing area. The method includes outputting, via a transducer, an ultrasonic pulse through the fluid, receiving, via the transducer, an echo of the ultrasonic pulse, and determining, via a controller, a time-of-flight of the ultrasonic pulse. The method also includes receiving, via a temperature sensor, a temperature of the fluid and determining, via the controller, a characteristic of the fluid based on the time-of-flight and the temperature. The method also includes comparing, via the controller, the characteristic of the fluid to a baseline characteristic, and outputting, from the controller, a signal based on the comparison between the characteristic and the baseline characteristic.

Another embodiment provides a method of determining whether a correct fluid is within a tank at a fluid change interval. The method includes determining, via a controller, if the fluid within the tank has been changed, and determining, via the controller, a characteristic of the fluid. The method includes, comparing, via the controller, the characteristic of the fluid to a baseline characteristic, and outputting, from the controller, a signal based on the comparison between the characteristic of the fluid and the baseline characteristic.

Another embodiment provides a method of sensing a fluid. The method includes transmitting, via a transducer, a first ultrasonic pulse through a portion of the fluid toward a reflector and receiving, via the transducer, a first echo of the first ultrasonic pulse, wherein the first ultrasonic pulse is transmitted and the first echo is received within a first time period. The method also includes determining a first measurement of the first ultrasonic pulse, and determining, via a temperature sensor, a first temperature, the first temperature determined at the first time period. The method includes transmitting, via the transducer, a second ultrasonic pulse through the portion of the fluid toward the reflector and receiving, via the transducer, a second echo of the first ultrasonic pulse, wherein the second ultrasonic pulse is transmitted and the second echo is received within a second time period. The method includes determining a second measurement of the second ultrasonic pulse and determining, via the temperature sensor, a second temperature, the second temperature determined at the second time period. The method includes determining, via a controller, a slope based on the first measurement, the second measurement, the first temperature, and the second temperature, and comparing, via the controller, at least one selected from the group consisting of the slope to a predetermined slope and the first measurement to a predetermined measurement.

Other aspects, features, and advantages of various embodiments will become apparent by consideration of the detailed description and accompanying drawings.

DETAILED DESCRIPTION

Before any embodiments are explained in detail, it is to be understood that the invention is not limited in its application to the details of construction and the arrangement of components set forth in the following description or illustrated in the following drawings. Other embodiments and ways of being practiced or of being carried out are possible.

Figure 1:
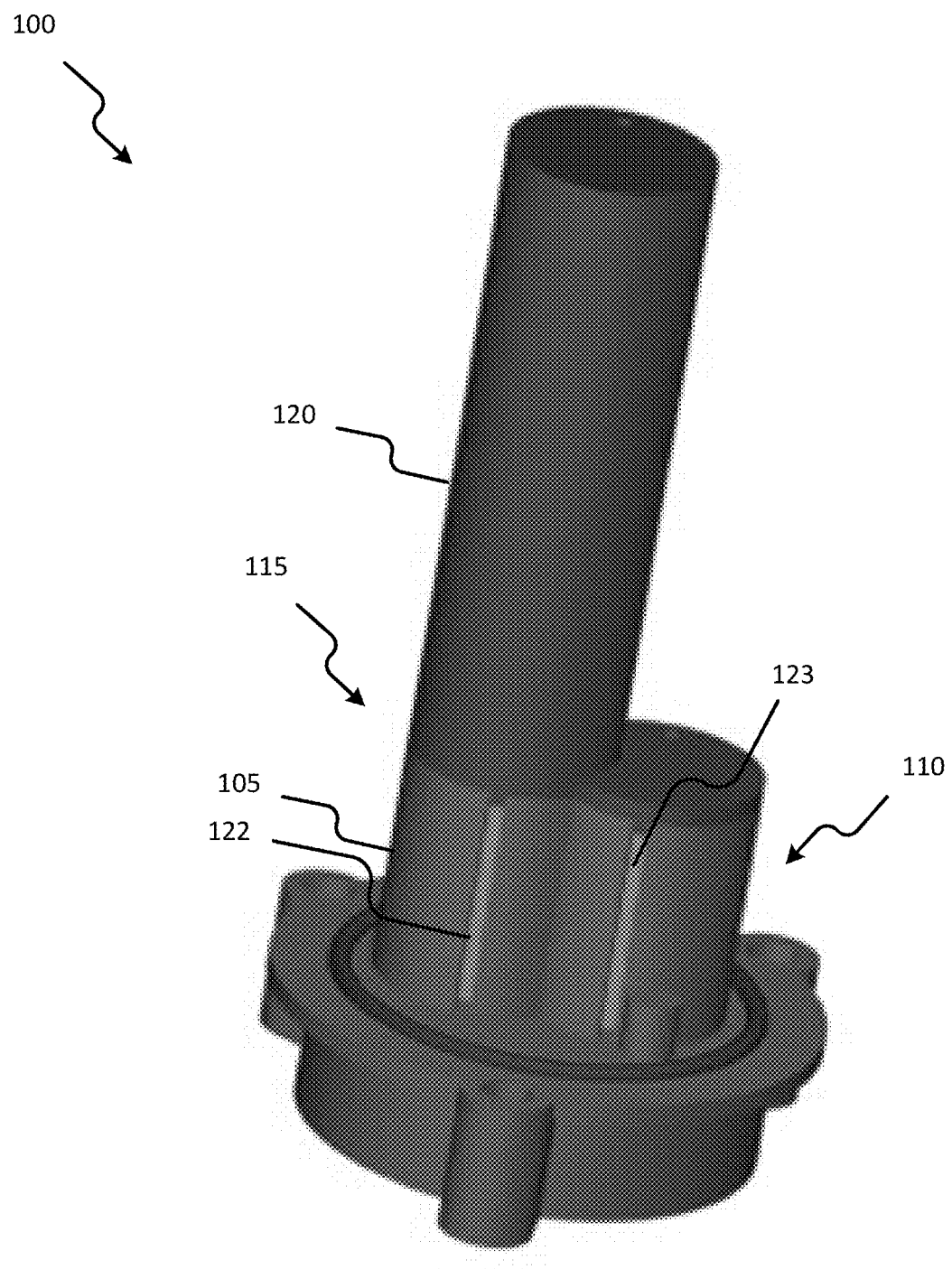
FIG. 1 is a perspective view of a system according to some embodiments.

FIG. 1 illustrates a perspective view of a system or sensing system 100 according to some embodiments. In some embodiments, the sensing system 100 is placed within a tank. In certain instances, the sensing system 100 is placed on a bottom of the tank. However, the sensing system 100 may be positioned at different locations. The sensing system 100 senses one or more characteristics of a fluid (for example, oil, fuel, diesel exhaust fluid, brake fluid, transmission fluid, washer fluid, refrigerant, etc.) contained within the tank. The sensing system 100 includes a housing 105, a level sensor 115, and a viscosity sensor 110. In some embodiments, the level sensor 115 includes a focus tube 120. The housing 105 may be formed or otherwise constructed from a plastic or similar material. In some embodiments, including the one illustrated, the housing 105 includes a level gap 122 and a viscosity gap 123. The level gap 122 allows the fluid to flow into the level sensor 115 of the sensing system 100 while the viscosity gap 123 allows the fluid to flow into the viscosity sensor 110 of the sensing system 100.

Figure 2:
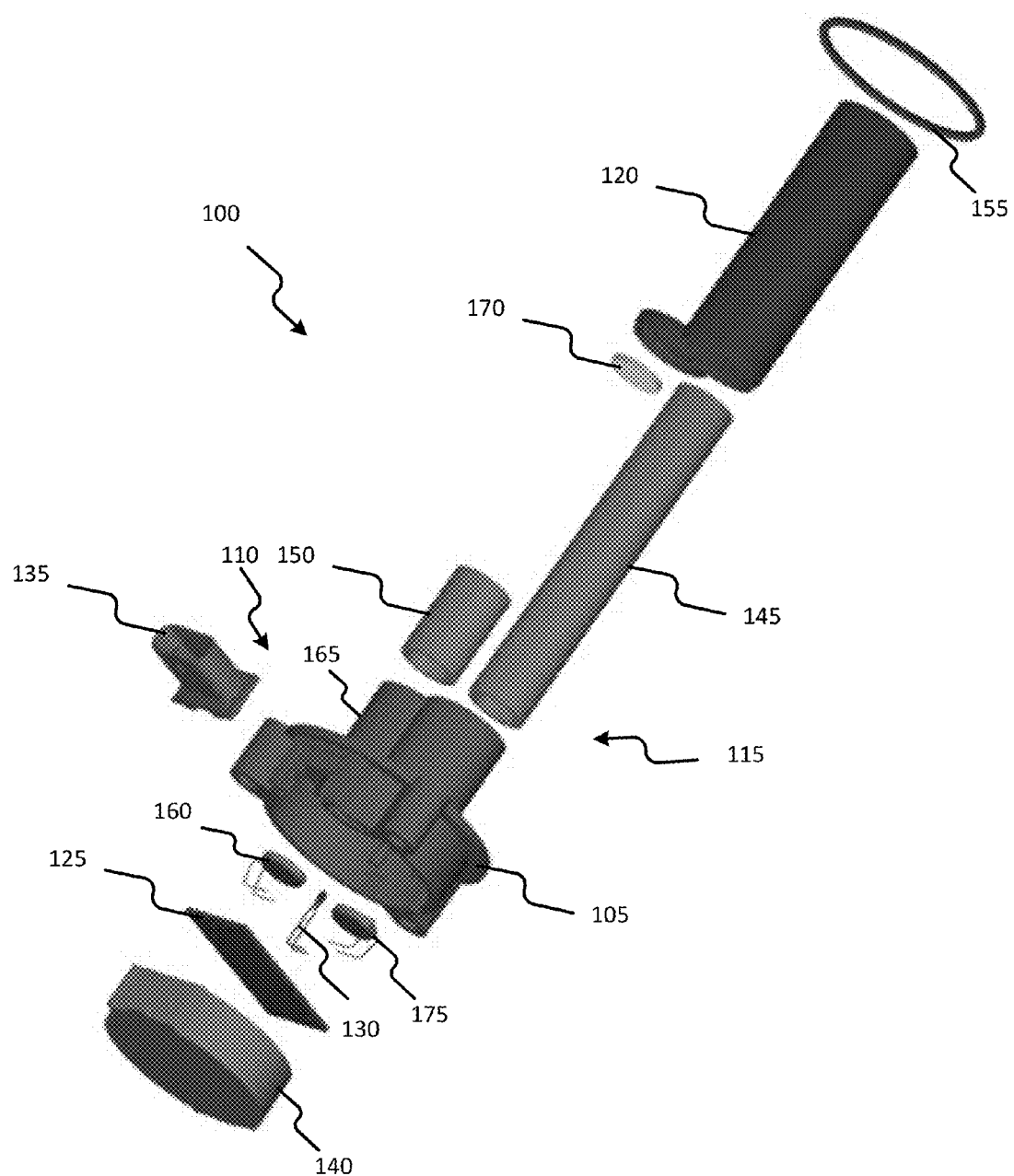
FIG. 2 is an exploded view of the system of FIG. 1 according to some embodiments.
Figure 3:
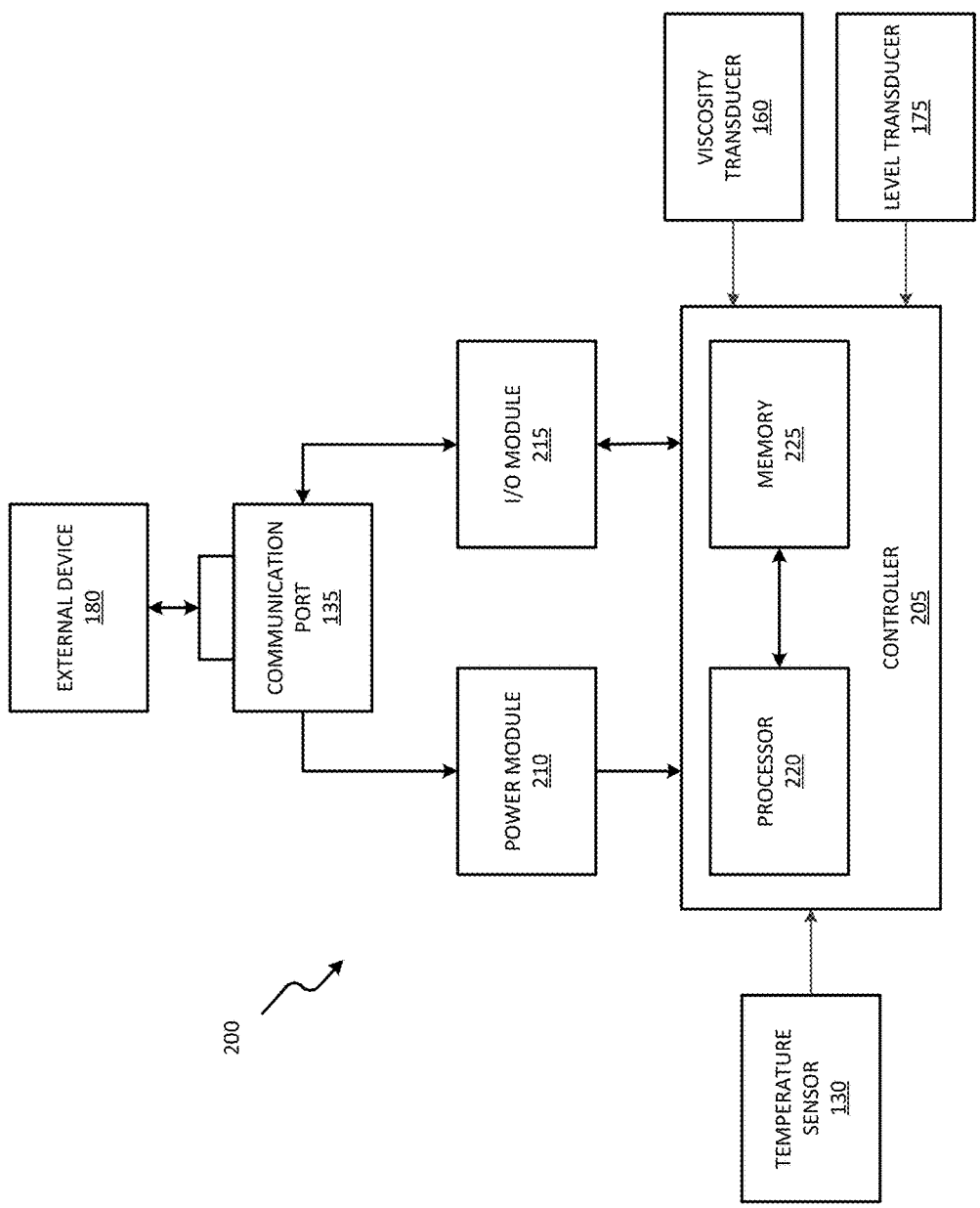
FIG. 3 is a block diagram of a control system of the system of FIG. 1 according to some embodiments.

FIG. 2 illustrates an exploded view of the sensing system 100 according to some embodiments. The sensor 100 includes a printed-circuit board (PCB) 125 and a plurality of sensors (i.e., sensing elements). In the illustrated embodiment, the plurality of sensors include the viscosity sensor 110, the level sensor 115, and a temperature sensor 130. In other embodiments, the sensing system 100 may include more or fewer sensors than shown in the illustrated embodiment. Each of the plurality of sensors is electrically coupled to the PCB 125. In some embodiments, the PCB 125 includes a sensor control system 200 (FIG. 3), which, among other things, provides power to the plurality of sensors, analyzes data from the plurality of sensors, and outputs the analyzed data to other components such as an external device 180 (FIG. 3). As illustrated in FIG. 2, the sensing system 100 also includes a communication port 135, potting 140, a level aeration filter 145, a viscosity aeration filter 150, and a seal 155. The potting 140 is a potting material used to support and/or protect the PCB 125 as well as other circuitry and components of the sensing system 100.

In some embodiments, the sensing system 100 is configured to be mounted through an opening in a bottom of the tank. In such an embodiment, the seal 155 prevents the fluid from leaking through the coupling between the sensing system and tank. The seal 155 may be formed or otherwise constructed from a rubber or similar material.

The viscosity sensor 110 is a viscosity sensing element for determining a viscosity of the fluid contained within the tank. The viscosity sensor 110 includes a viscosity transducer 160, a viscosity measurement channel 165, and a viscosity reflector 170. The viscosity transducer 160 is a sensing element configured to act as both a transmitter and receiver. In some embodiments, the viscosity transducer 160 is a piezoelectric transducer. The viscosity measurement channel 165 acts as a sensing area and helps containing the fluid to be sensed. In operation, the viscosity transducer 160 generates an acoustic wave signal (for example, an ultrasonic pulse), which propagates through the fluid contained within the viscosity measurement channel 165, toward the viscosity reflector 170. The acoustic wave signal reflects off of the viscosity reflector 170 and travels back toward the viscosity transducer 160. The time-of-flight (ToF) of the acoustic wave signal (from the viscosity transducer 160 to the reflector 170 and back to the viscosity transducer) is output to the sensor control system 200 of the sensing system 100.

The level sensor 115 is a level sensing element for determining a level, and thus a quantity, of the fluid within the tank. In the illustrated embodiment, the level sensor 115 includes a level transducer 175, which may be, for example, a piezoelectric transducer. The level sensor 115 also includes the focus tube 120 (for example, a sensing tube). The level transducer 175 is configured to act as both a transmitter and receiver. The focus tube 120 acts as a sensing area and helps contain a fluid to be sensed. Some embodiments of the level sensor 115 may also include a float. The float floats on a surface 315 (FIG. 4) of the fluid contained within the tank. The level transducer 175 generates an acoustic wave signal (for example, an ultrasonic pulse), which propagates through the fluid contained within the focus tube 120. The acoustic wave signal propagates toward a surface 315 of the fluid, or the float. The acoustic wave signal reflects off of the surface 315, or the float, and travels back toward the level transducer 175. The ToF of the acoustic wave signal is output to the sensor control system 200. In some embodiments, the ToF of the acoustic wave signal is converted into a level measurement. In such an embodiment, the conversion may be performed based on a known speed-of-sound of the fluid. In some embodiments, the conversion is performed using a look up table.

The temperature sensor 130 is a temperature sensing element for determining a temperature of the fluid within the tank. In one embodiment the temperature sensor 130 is a thermocouple. In another embodiment, the temperature sensor 130 is a thermistor. In yet another embodiment, the temperature sensor 130 is a resistance temperature sensor. In yet another embodiment, the temperature sensor 130 is an infrared temperature sensor. The temperature sensor 130 outputs the sensed temperature to the controller 205. In some embodiments, the level sensor 115 and the temperature sensor 130 are combined into a combination sensor capable of sensing both a level and a temperature. In some embodiments, the viscosity sensor 110 and the temperature sensor 130 are combined into a combination sensor capable of sensing both a concentration and a temperature of the fluid. In other embodiments, the viscosity sensor 110, the level sensor 115, and the temperature sensor 130 are combined into a combination sensor capable of sensing all three metrics.

The communication port 135 provides communication between the sensing system 100 and an external device 180 (FIG. 3). In some embodiments, the external device 180 is a computer and/or control system of a motor vehicle. In such an embodiment, the communication port 135 may be in the form of a digital port, such as a port compliant with the J1939 or CAN standards. The communication port 135 provides a mechanism for communicating with the vehicle's data bus. In other embodiments, the communication port 135 may communicate with the external device 180 using a suitable analog or digital signal, depending on the needs of the specific application. In some embodiments, the external device 180 is a computing device, for example, a desktop computer, a laptop computer, a smart phone, or a tablet computer.

The level aeration filter 145 and the viscosity aeration filter 150 are configured to filter a gas portion of the fluid from entering the focus tube 120 and the viscosity measurement channel 165, respectively, while allowing a liquid portion of the fluid to enter these components. In some embodiments, the gas portion of the fluid includes one or more air bubbles. In some embodiments, the level aeration filter 145 and the viscosity aeration filter 150 comprise a mesh material. In some embodiments, the mesh material is a synthetic polymer (for example, nylon, polyethylene, polypropylene, etc.). In other embodiments, the mesh material is a metal.

FIG. 3 illustrates a block diagram of a control system 200 of the sensing system 100. In some embodiments, the control system 200 is contained, partially or completely, on the PCB 125. The control system 200 includes a controller 205, a power module 210, and an input/output (I/O) module 215. The controller 205 includes a processor 220 and memory 225. The memory 225 stores instructions executable by the processor 220. In some instances, the controller 205 includes one or more of a microprocessor, digital signal processor (DSP), field programmable gate array (FPGA), application specific integrated circuit (ASIC), or the like. The control system 200, via the controller 205, is communicatively coupled to the viscosity sensor 110, the level sensor 115, and the temperature sensor 130.

The power module 210 receives power and outputs a nominal power to the controller 205. In the illustrated embodiment, the power module 210 receives power from the external device 180, via the communication port 135. In other embodiments, the power module 210 may receive power from another power sources, such but not limited to, a battery and/or a renewable power source. The I/O module 215 provides wired and/or wireless communication between controller 205 and the external device 180.

Figure 4:
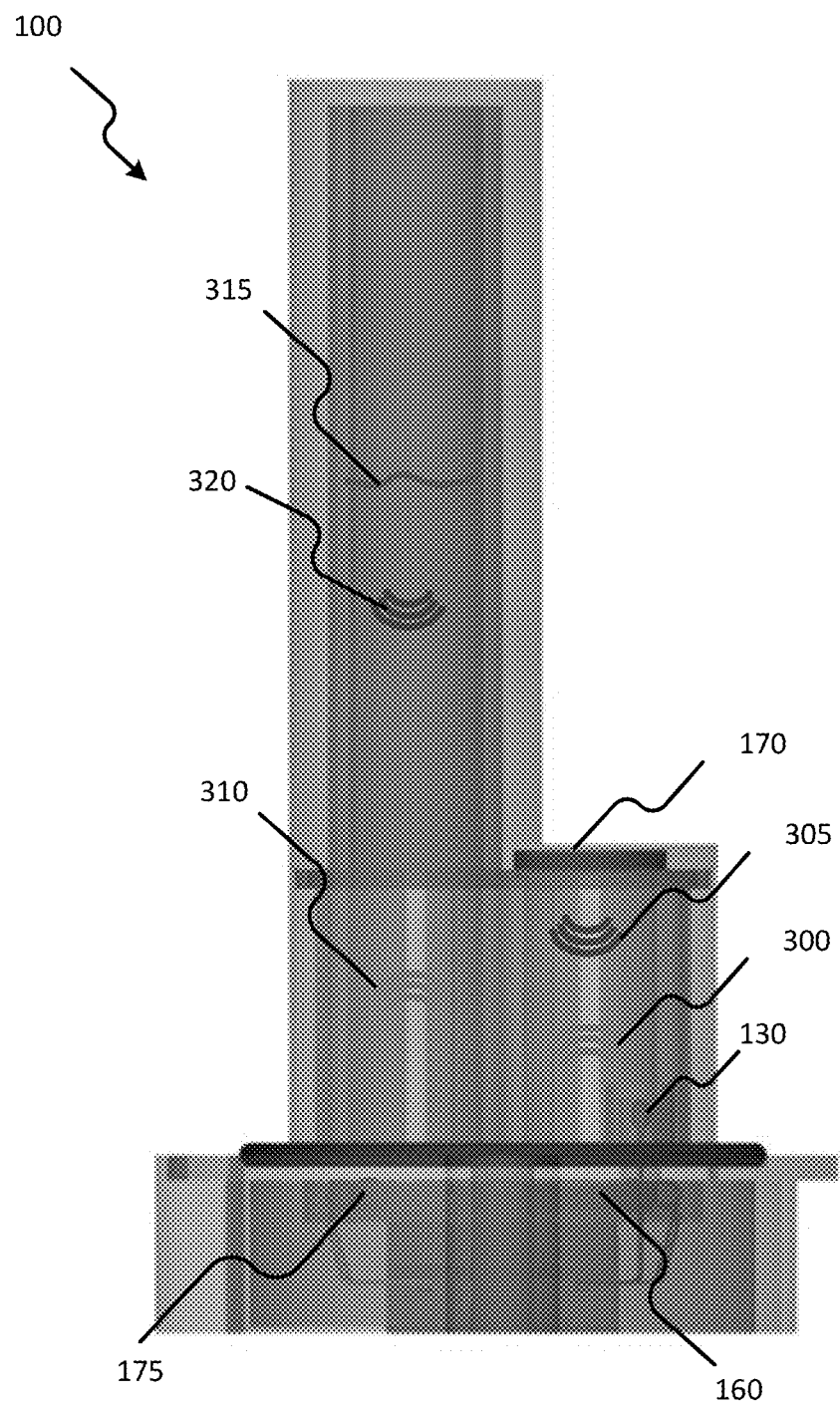
FIG. 4 is a partially transparent view of the system of FIG. 1 according to some embodiments.

FIG. 4 is a partially transparent view of the sensing system 100 according to some embodiments. In operation, the controller 205 controls the viscosity transducer 160 to output an acoustic signal 300 toward the reflector 170. The acoustic signal 300 reflects off of the reflector 170 and travels back toward the viscosity transducer 160 as an acoustic echo 305. The controller 205 determines a viscosity time-of-flight based on the output viscosity acoustic signal 300 and the received acoustic echo 305. The controller 205 also receives a temperature of the fluid from the temperature sensor 130. In some embodiments, the controller 205 also determines a speed-of-sound of the fluid based on the viscosity time-of-flight and the temperature of the fluid. The controller 205 also controls the level transducer 175 to output a level acoustic signal 310 toward the surface 315 of the fluid. The level acoustic signal 310 reflects off of the surface 315 and travels back toward the level transducer 175 as a level acoustic echo 320. The controller 205 determines a level time-of-flight based on the output level acoustic signal 310 and the received level acoustic echo 320. In some embodiments, the controller 205 determines a level of the fluid based on the level time-of-flight and the speed-of-sound of the fluid. The controller 205 determines one or more characteristics of the fluid based on the viscosity time-of-flight, the speed-of-sound of the fluid, and/or the temperature. The characteristics may include a grade of the fluid, a brand of the fluid, a kinematic viscosity of the fluid, a quality of the fluid, and a level of the fluid. In some embodiments, the controller 205 outputs a signal to the external device 180 based on the one or more characteristics.

Figure 5A:
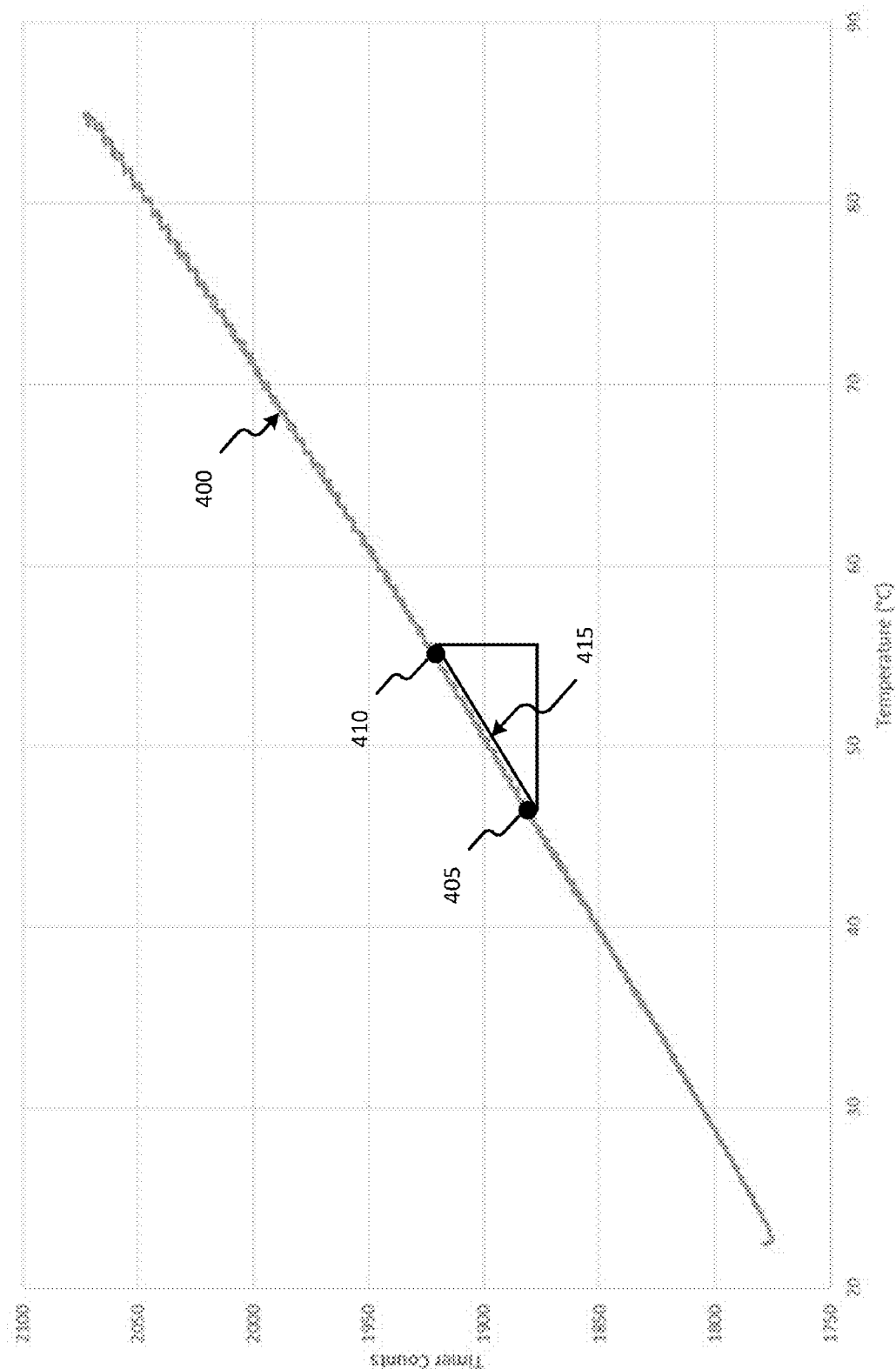
FIGS. 5A through 5E are charts illustrating baseline indexes of a fluid sensed by the system of FIG. 1 according to some embodiments.

FIG. 5A is a chart illustrating an index 400 corresponding to a fluid. The index 400 corresponds to a characteristic of a fluid. The index 400 may correspond to a grade, a brand, a viscosity, or a quality. In the example illustrated, index 400 includes a plurality of points, including a first point 405 and a second point 410. First point 405 corresponds to a point on index 400 at a first time-of-flight and a first temperature. Second point 410 corresponds to a point on index 400 at a second time-of-flight and a second temperature. In other embodiments, the first time-of-flight and the second time-of-flight are determined based on a time-of-flight of an ultrasonic pulse output toward a reflector, reflected off of the reflector, and returned as an echo. In some embodiments, the first time-of-flight and the second time-of-flight may be viscosity time-of-flights discussed above.

A slope, or rate of change, 415 may be calculated based on the first point 405 and the second point 410. In some embodiments, the slope is determined using Equation 1 below.

$$\text{Slope} = \frac{ToF_2 - ToF_1}{T_2 - T_1} \quad [1]$$

In Equation 1, $ToF_1$ corresponds to the first time-of-flight, $ToF_2$ corresponds to the second time-of-flight, $T_1$ corresponds to the first temperature, and $T_2$ corresponds to the second temperature. The first time-of-flight and the second time-of-flight are measurements of the first and second ultrasonic pulses.

Figure 5B:
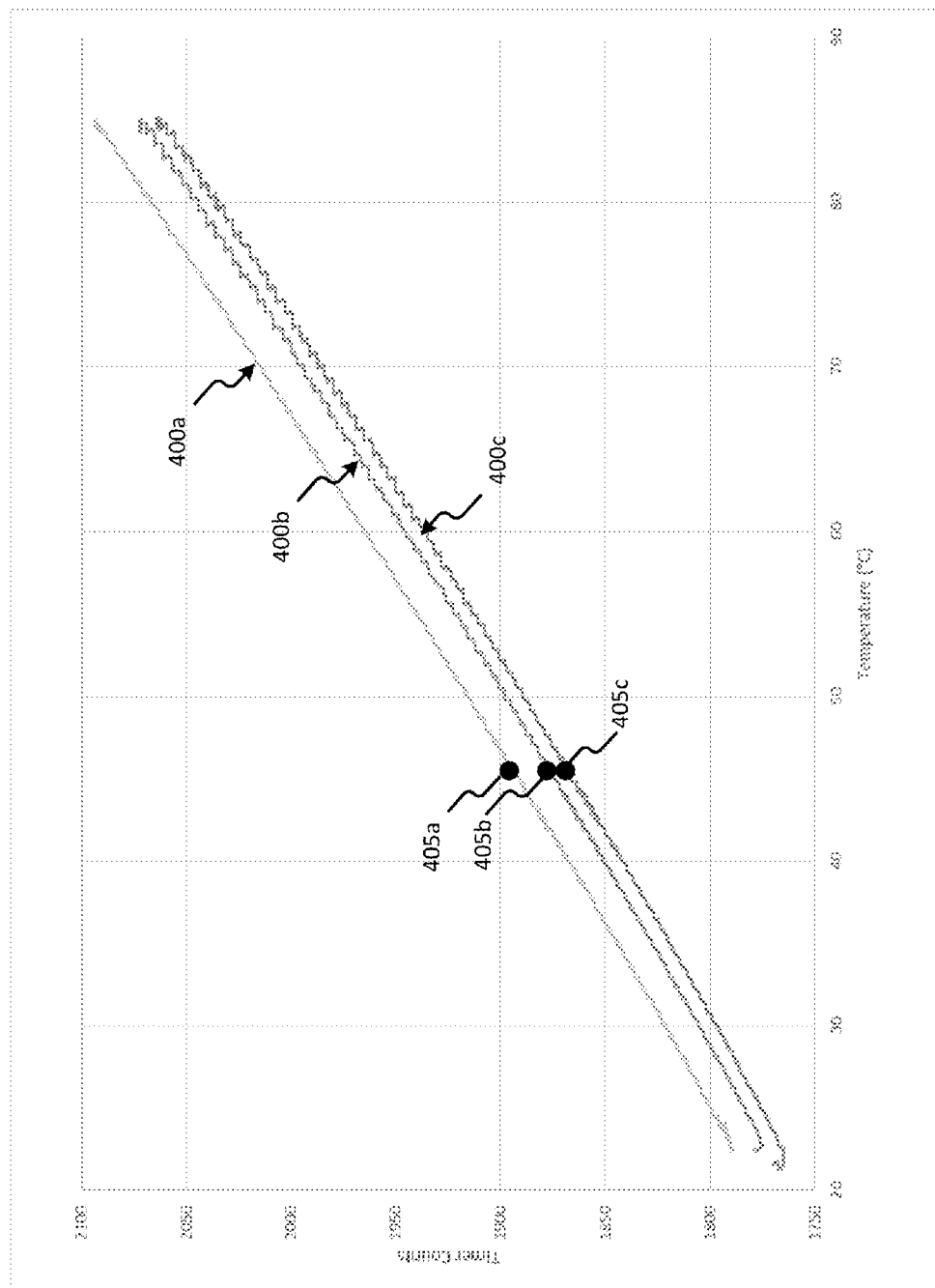

FIG. 5B is a chart illustrating a plurality of example indexes 400a through 400c corresponding to a plurality of fluids. As illustrated, index 400a includes a first point 405a, index 400b includes a first point 405b, and index 400c includes a first point 405c. In the illustrated embodiment, first points 405a through 405c corresponds to a first temperature (for example approximately 45° C.), with each baseline index 400a through 400c having a respective time-of-flight at the respective first temperature. As illustrated, the three indexes 400a through 400c have substantially similar slopes. However, the three fluids corresponding to indexes 400a through 400c may be distinguished from each other based on their respective time-of-flights at the first temperature.

Figure 5C:
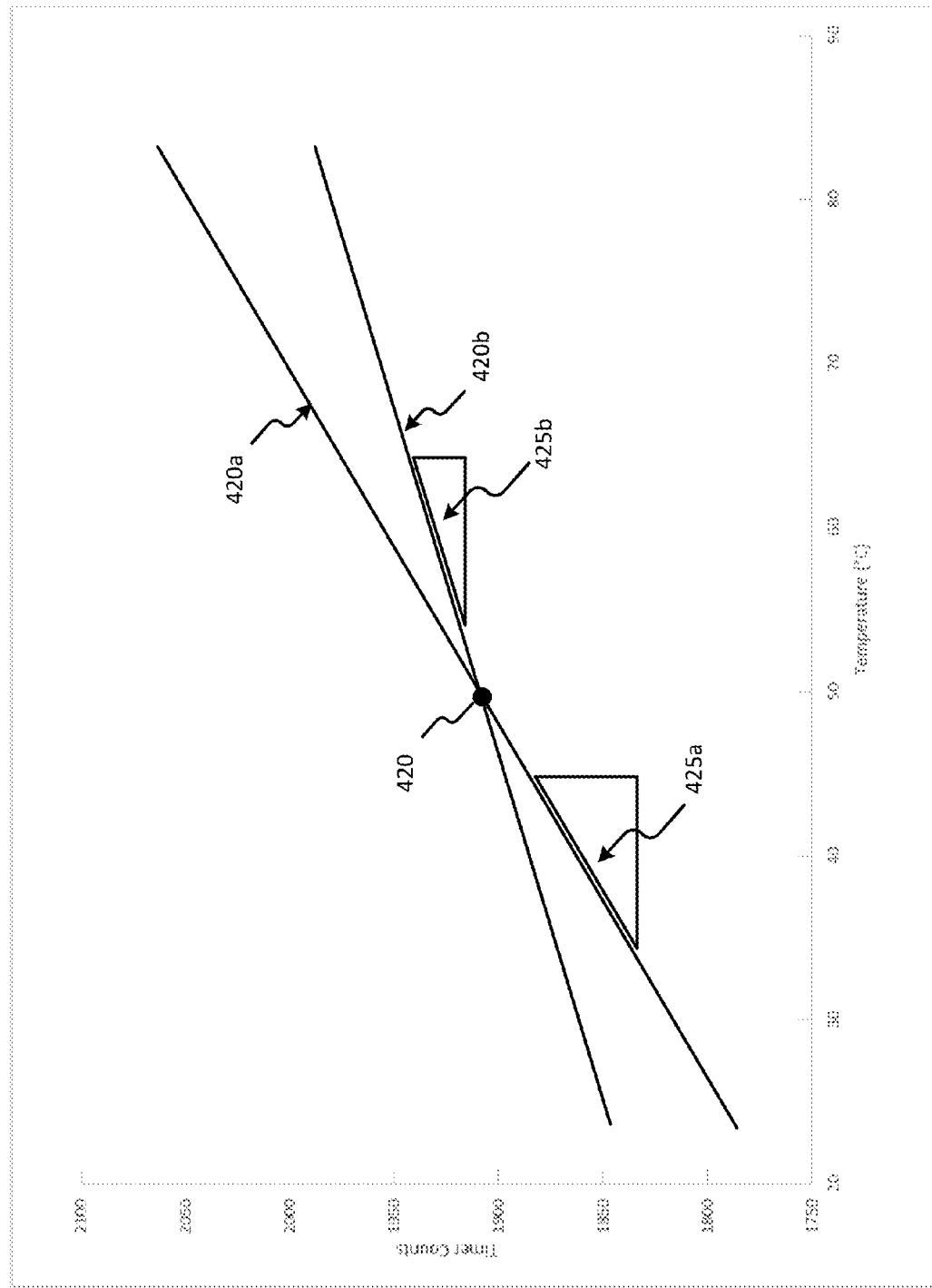

FIG. 5C is a chart illustrating example indexes 420a and 420b corresponding to respective fluids. In the example provided, indexes 420a and 420b share a point 425 at a first temperature. However, the two fluids corresponding to baseline indexes 420a and 420b may be distinguished from each other based on their respective slopes 430a and 430b.

Figure 5D:
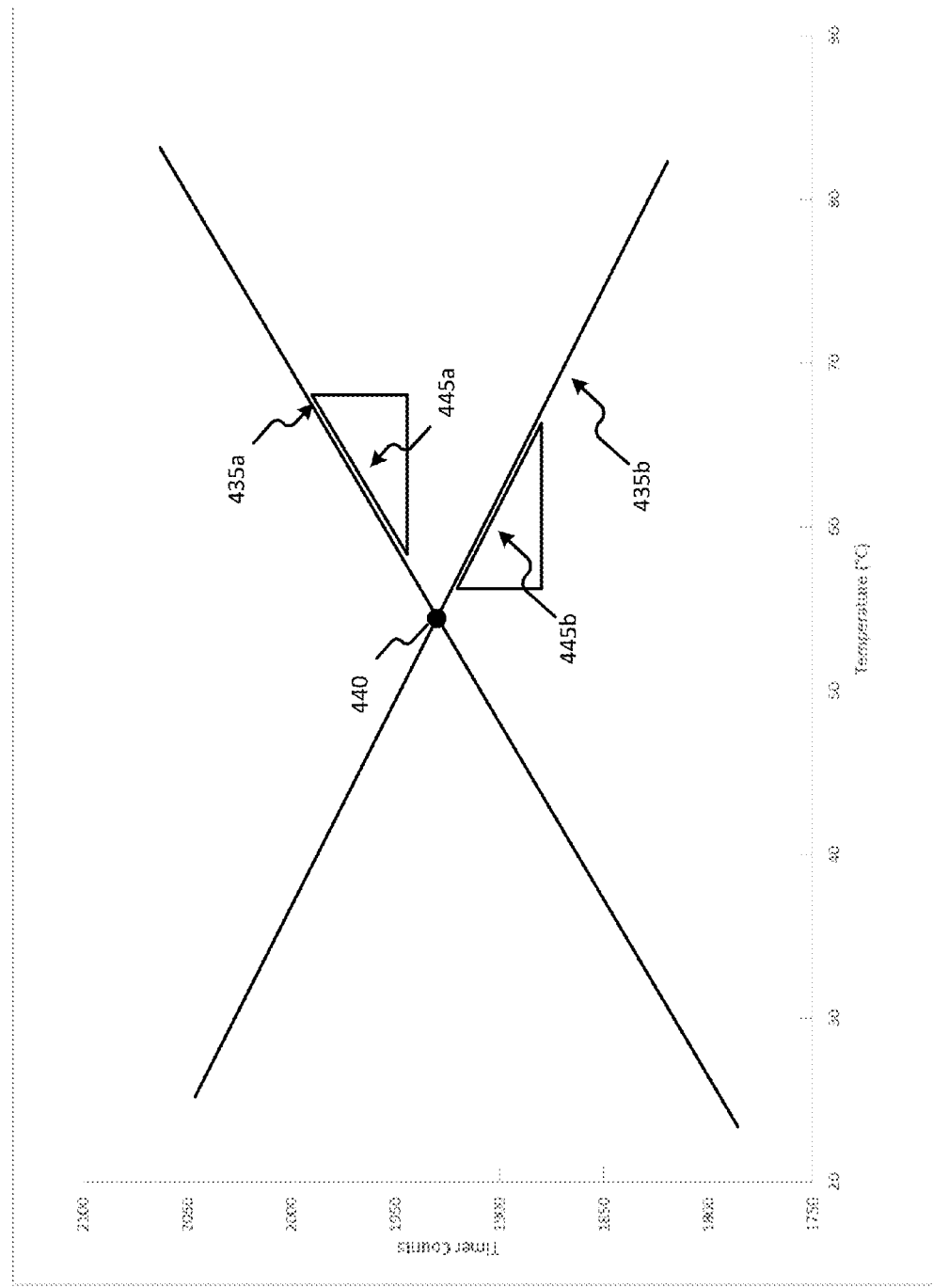

FIG. 5D is a chart illustrating indexes 435a and 435b corresponding to respective fluids. Indexes 435a and 435b share a point 440 at a first temperature. Additionally, a first slope 445a of the first index 435a has a substantially similar magnitude as a second slope 445b of the second index 435b. However, the two fluids corresponding to indexes 435a and 435b may be distinguished from each other based on the sign (for example, negative or positive) of their respective slopes 445a and 445b.

Figure 5E:
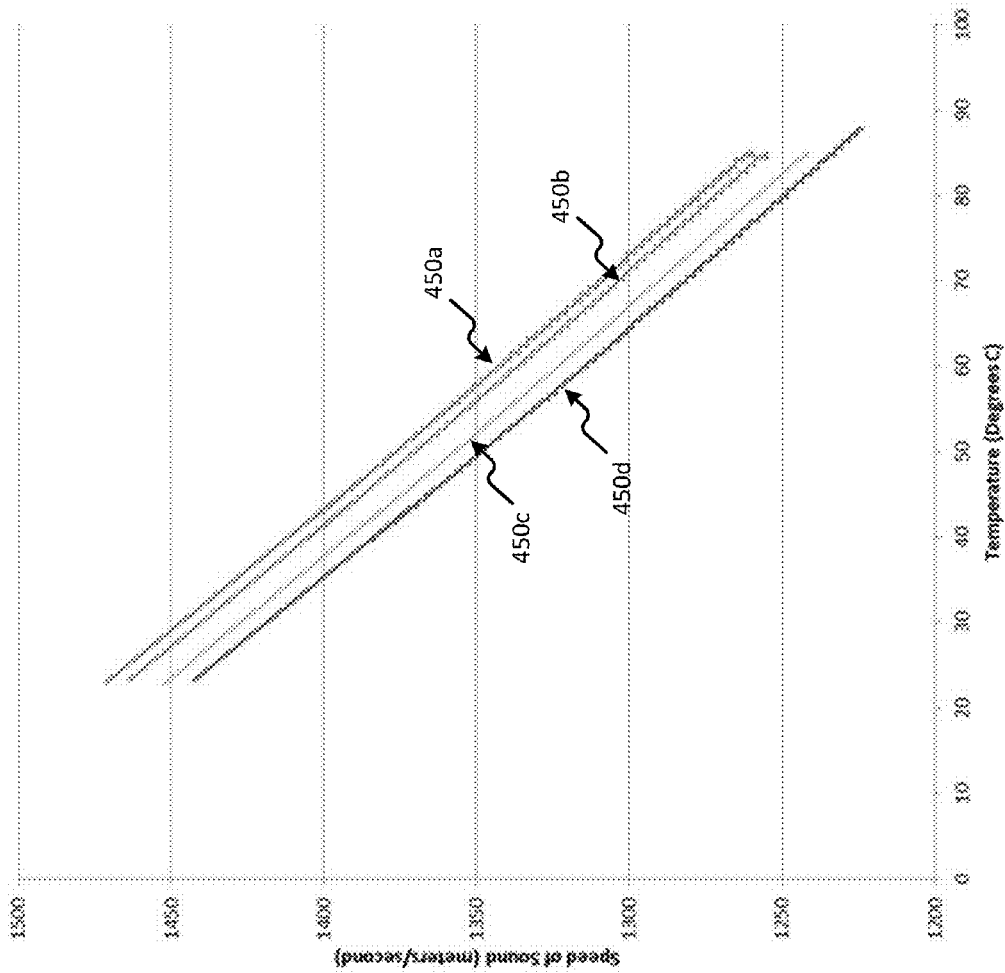

A fluid, or characteristic of a fluid, may be identified by determining a first point along an index, a second point along an index, and/or a slope, or rate of change, of an index, as is illustrated in FIGS. 5A through 5D. In the embodiment shown, the indexes are calculated based on a baseline viscosity time-of-flight (for example, an initial viscosity time-of-flight) and a temperature (for example, an initial temperature). However, as illustrated in FIG. 5E, in other embodiments, the indexes (for example indexes 450a through 450d) may be calculated based on a speed-of-sound and a temperature. In such an embodiment, the slope may be determined using Equation 2 below.

$$\text{Slope} = \frac{SoS_2 - SoS_1}{T_2 - T_1} \quad [2]$$

In Equation 2, $SoS_1$ corresponds to a first speed-of-sound, $SoS_2$ corresponds to a second time-of-flight speed-of-sound, $T_1$ corresponds to the first temperature, and $T_2$ corresponds to the second temperature. The first speed-of-sound and the second speed-of-sound are measurements of the first and second ultrasonic pulses.

In some embodiments, the indexes are calculated by the controller 206. In some embodiments, the indexes are predetermined and known as baseline indexes. In such an embodiment, one or more baseline indexes of known fluids may be stored in the memory 225 of the controller 205 or the external computer 180. In such an embodiment, a calculated index of a fluid stored in the tank may be compared to the one or more baseline indexes of known fluids. In the example provided, the baseline indexes are illustrated as curves on graphs. However, in other embodiments, the baseline indexes may be stored as values in tables.

Figure 6:
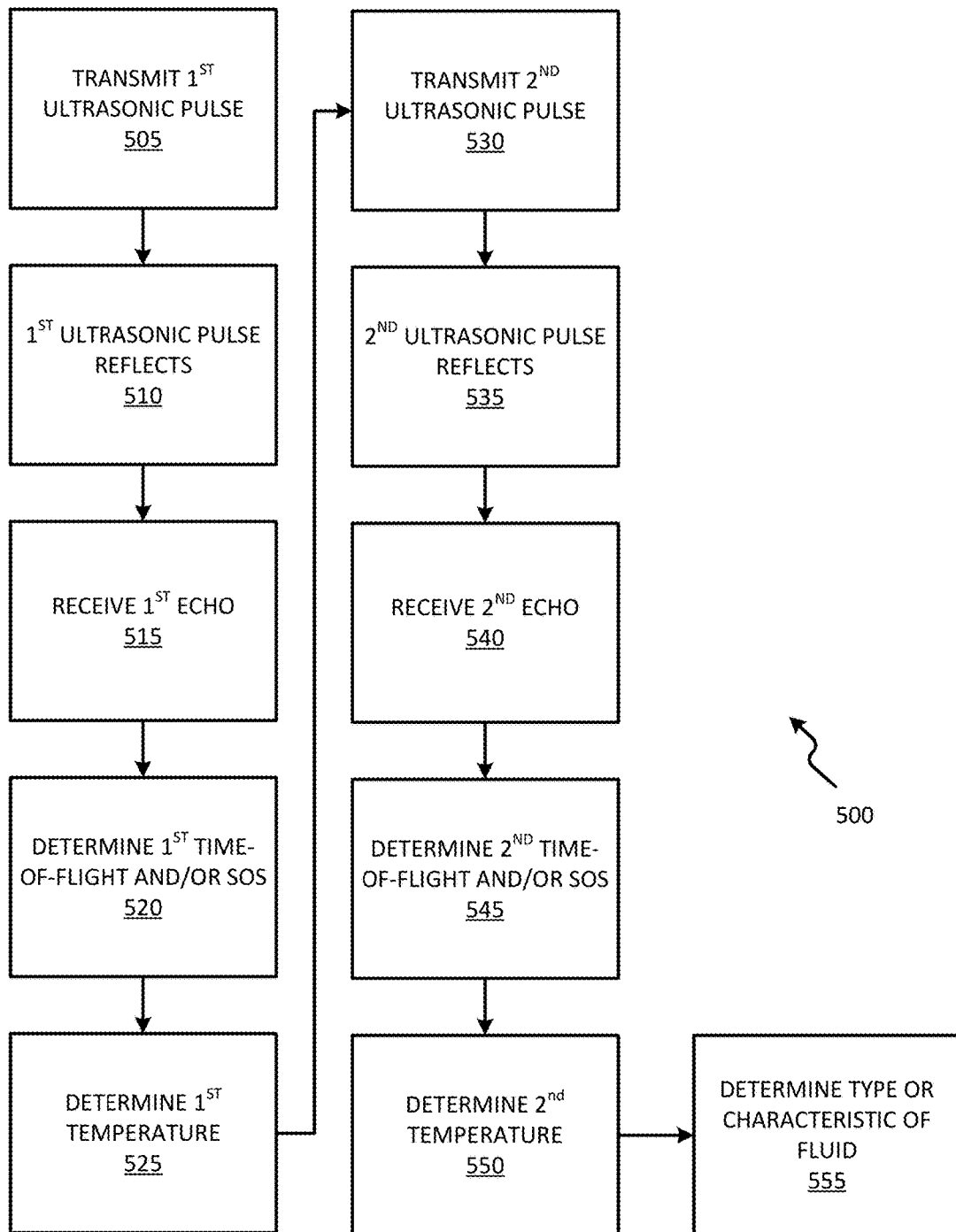
FIG. 6 is a flow chart illustrating operation of the system of FIG. 1 according to some embodiments.

FIG. 6 is a flow chart illustrating an operation, or process, 500 according to one embodiment for determining a fluid type, or a characteristic of a fluid (for example, a grade of the fluid, a brand of the fluid, a viscosity of the fluid, and a quality of the fluid), within the tank. The method 500 may also be used to determine whether a correct fluid is within the tank. It should be understood that the order of the steps disclosed in process 500 may vary, additional steps may be added, and not all of the steps may be required. The sensing system 100 transmits a first ultrasonic pulse into a portion of the fluid toward the reflector 170 (block 505). The first ultrasonic pulse is reflected off of the reflector 170 as a first echo (block 510). The sensing system 100 receives the first echo of the first ultrasonic pulse (block 515). In some embodiments, the first ultrasonic pulse is transmitted and received by the viscosity transducer 160. The sensing system 100 determines a first measurement (for example, a first time-of-flight or a first speed-of-sound) of the first ultrasonic pulse (block 520). The sensing system 100 determines, via temperature sensor 130, a first temperature of the fluid (block 525). In some embodiments, the first ultrasonic pulse is transmitted, the first echo is received, and the first temperature is determined within a first time period.

The sensing system 100 transmits a second ultrasonic pulse into the portion of the fluid toward the reflector 170 (block 530). The second ultrasonic pulse is reflected off of the reflector 170 as a second echo (block 535). The sensing system 100 receives the second echo of the second ultrasonic pulse (block 540). In some embodiments, the first ultrasonic pulse is transmitted and received by the viscosity transducer 160. The sensing system 100 determines a second measurement (for example, a second time-of-flight or a second speed-of-sound) of the second ultrasonic pulse (block 545). The sensing system 100 determines, via temperature sensor 130, a second temperature of the fluid (block 550). In some embodiments, the second ultrasonic pulse is transmitted, the second echo is received, and the second temperature is determined within a second time period. The sensing system 100 determines the type of fluid, or a characteristic of the fluid, using the first measurement at the first temperature, the second measurement at the second temperature, and/or the slope, or rate of change, of the first measurement and the second measurement (block 555).

In some embodiments, the type of fluid, or characteristic of the fluid, is determined by comparing the first measurement at the first temperature, the second measurement at the second temperature, and/or the slope to one or more predetermined measurements and/or slopes of known fluids. In such an embodiment, a signal is output when the first measurement and/or slope deviates (for example, by a predetermined deviation) from an expected predetermined measurement and/or slope. In such an embodiment, the deviation may vary based on the determined viscosity time-of-flight and the temperature. In another embodiment, the predetermined deviation is based on a user input. In other embodiments, a signal is output when the first measurement at the first temperature, the second measurement at the second temperature, and/or the slope is substantially equivalent to a predetermined measurement and/or slope of a known fluid.

Figure 7:
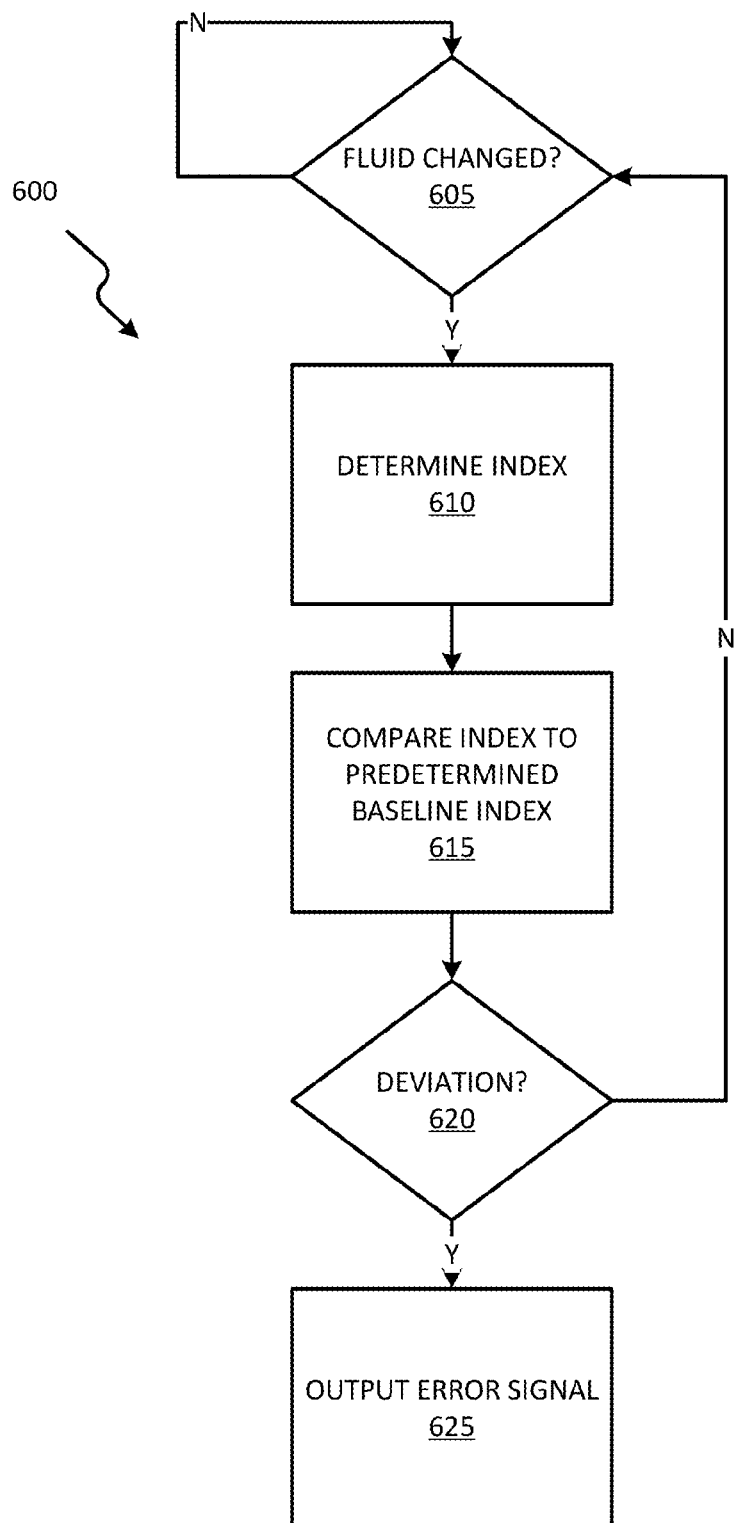
FIG. 7 is a flow chart illustrating operation of the system of FIG. 1 according to some embodiments.

FIG. 7 is a flow chart illustrating an operation, or process, 600 of the sensing system 100 according to some embodiments. It should be understood that the order of the steps disclosed in process 600 could vary. Furthermore, additional steps may be added to the process and not all of the steps may be required. The sensing system 100 determines that fluid in the tank has been changed (block 605). In some embodiments, the sensing system 100 determines the fluid in the tank has been changed by receiving an indication (for example, a fluid change signal) from the user (for example, through the external device 180). In other embodiments, the sensing system 100 determines that the fluid in the tank has been changed by determining that there has been an addition of fluid. In such an embodiment, the sensing system 100 may compare a level (for example, a level time-of-flight) to a previously-determined level (for example, a previously-determined level time-of-flight). If the level is greater than the previously-determined level, the sensing system 100 determines that fluid has been added, or changed.

When the sensing system 100 determines that fluid in the tank has been changed, the sensing system 100 determines an index of the fluid (block 610). The sensing system 100 compares the index to a predetermined baseline index (block 615). When the index deviates from the predetermined baseline index, the sensing system 100 outputs an error signal or similar message to the external device 180 (block 625). When the index does not deviates from the predetermined baseline index, the process 600 cycles back to block 605.

Figure 8:
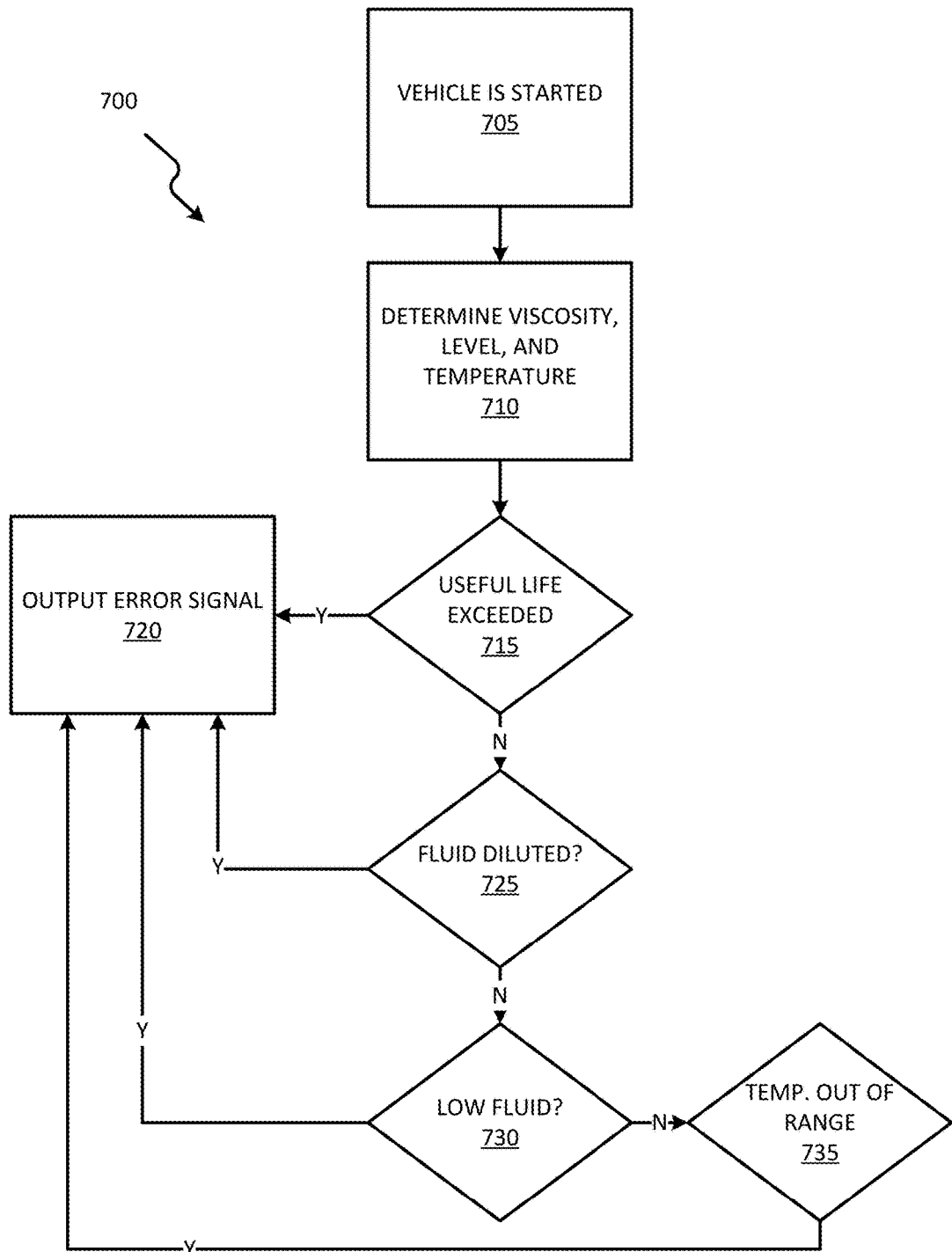
FIG. 8 is a flow chart illustrating operation of the system of FIG. 1 according to some embodiments.

FIG. 8 is a flow chart illustrating an operation, or process, 700 of the sensing system 100 according to some embodiments. It should be understood that the order of the steps disclosed in process 700 could vary. Furthermore, additional steps may be added to the process and not all of the steps may be required. The engine of the motor vehicle is started (block 705). The sensing system 100 determines a viscosity, a level, and a temperature of the fluid (block 710).

The sensing system 100 determines if a useful fluid life has been exceeded (block 715). In some embodiments, the sensing system 100 determines if the useful fluid life has been exceeded by comparing the viscosity to a baseline viscosity (for example, by using a predetermined baseline index). If the viscosity is greater than a predetermined range above the baseline viscosity, the sensing system 100 determines that the useful fluid life has been exceeded. When the useful fluid life has been exceeded, the sensing system 100 outputs an error signal or similar message to the external device 180 (block 720).

When the useful fluid life has not been exceeded, the sensing system 100 determines if the fluid has been diluted (block 725). In some embodiments, the sensing system 100 determines if the fluid has been diluted by comparing the viscosity to the baseline viscosity (for example, by using the predetermined baseline index). If the viscosity is lower than a predetermined range below the baseline viscosity, the sensing system 100 determines that the fluid has been diluted. When the fluid has been diluted, the sensing system 100 outputs an error signal or similar message to the external device 180 (block 720).

When the fluid has not been diluted, the sensing system 100 determines if there has been a loss of fluid, or low fluid (block 730). In some embodiments, the sensing system 100 determines if there is a loss of fluid, or low fluid, by comparing the level to a level threshold. In some embodiments, the level threshold is predetermined. If the level is less than the level threshold, the sensing system 100 determines that there has been a loss of fluid, or low fluid. When there is a loss of fluid, or low fluid, the sensing system 100 outputs an error signal or similar message to the external device 180 (block 720).

When the fluid is not low, the sensing system 100 determines if the temperature is outside of an a predetermined range (block 735). When the temperature is outside of the predetermined range, the sensing system 100 outputs an error signal or similar message to the external device 180 (block 720). When the temperature is within the predetermined range, process 700 cycles back to block 710.

In some embodiments, upon receiving the error signal, the external device 180 may initiate shut down of the engine of the motor vehicle. In other embodiments, upon receiving the error signal, the external device 180 may output an error indication to a user. Additionally, in some embodiments, the external device 180 may initiate shut down of the engine of the motor vehicle when the error indication is output a predetermined number of times.

Various features, aspects, and advantages of certain embodiments are set forth in the following claims.

What is claimed is:

1. A system for sensing characteristics of a fluid contained within a tank, the system comprising:
    an ultrasonic sensor configured to
        output a ultrasonic pulse into the fluid contained with the tank,
        receive an echo of the ultrasonic pulse, and
        output a signal based on the received echo;
    a temperature sensor configured to sense a temperature of the fluid contained within the tank and output a temperature signal corresponding to the temperature of the fluid contained within the tank; and
    a controller configured to determine whether the fluid in the tank has changed, and upon determining the fluid has changed:
        determine a time-of-flight based on the output of the ultrasonic pulse and the received echo of the ultrasonic pulse,
        receive the temperature signal,
        determine an index corresponding to a characteristic of the fluid contained within the tank based on the time-of-flight and the temperature signal,
        compare a slope of the index to a baseline slope of a baseline index, and
        output a signal based on the comparison between the slope of the index and the baseline slope of the baseline index.

2. The system of claim 1, wherein the baseline index corresponds to at least one baseline characteristic selected from a group consisting of a viscosity, a grade, a brand, and a quality, of a known fluid.

3. The system of claim 1, wherein the controller determines whether the fluid has been changed based on comparing a level to a previously-determined level.

4. The system of claim 1, wherein the controller determines whether the fluid has been changed based on receiving a fluid change signal.

5. The system of claim 1, wherein the characteristic is at least one characteristic selected from a group consisting of a grade, a brand, a kinematic viscosity, a quality, and a level.

6. The system of claim 1, wherein the system is coupled to a bottom of the tank.

7. The system of claim 1, further comprising an aeration filter.

8. The system of claim 7, wherein the aeration filter includes a mesh.

9. A method of sensing a characteristic of a fluid contained within a sensing area of a tank, the method comprising:
    determining whether the fluid in the tank has changed, and upon determining the fluid has changed:
        outputting, via a transducer, an ultrasonic pulse through the fluid;
        receiving, via the transducer, an echo of the ultrasonic pulse;
        determining, via a controller, a time-of-flight of the ultrasonic pulse;
        receiving, via a temperature sensor, a temperature of the fluid;
        determining, via the controller, an index corresponding to a characteristic of the fluid based on the time-of-flight and the temperature;
        comparing, via the controller, a slope of the index to a baseline slope of a baseline index; and
        outputting, from the controller, a signal based on the comparison between the slope of the index and the baseline slope of the baseline index.

10. The method of claim 9, wherein the baseline index corresponds to at least one baseline characteristic selected from a group consisting of a viscosity, a grade, a brand, and a quality, of a known fluid.

11. The method of claim 9, wherein the step of determining whether the fluid has been changed is based on comparing a level to a previously-determined level.

12. The method of claim 9, wherein the step of determining whether the fluid has been changed is based on receiving a fluid change signal.

13. The method of claim 9, wherein the characteristic is at least one characteristic selected from a group consisting of a grade, a brand, a kinematic viscosity, a quality, and a level.

* * * * *

UNITED STATES PATENT AND TRADEMARK OFFICE
CERTIFICATE OF CORRECTION

PATENT NO. : 10,422,732 B2  Page 1 of 1
APPLICATION NO. : 15/238936
DATED : September 24, 2019
INVENTOR(S) : Gregory P. Murphy and Mark Edward Kernien It is certified that error appears in the above-identified patent and that said Letters Patent is hereby corrected as shown below:

In the Claims

Column 9, Line 33-34, Claim 1, please replace "output a ultrasonic pulse into the fluid contained with the tank," with --output an ultrasonic pulse into the fluid contained within the tank,--

Signed and Sealed this
Fifth Day of January, 2021

Andrei Iancu
*Director of the United States Patent and Trademark Office*